US012606509B2

(12) United States Patent
Abdur-Rashid et al.

(10) Patent No.: US 12,606,509 B2
(45) Date of Patent: Apr. 21, 2026

(54) CATALYTIC CANNABIGEROL PROCESSES AND PRECURSORS

(71) Applicant: KARE CHEMICAL TECHNOLOGIES INC., Mississauga (CA)

(72) Inventors: Kamaluddin Abdur-Rashid, Mississauga (CA); Wenli Jia, Toronto (CA); Kareem Abdur-Rashid, Mississauga (CA)

(73) Assignee: KARE CHEMICAL TECHNOLOGIES INC., Mississauga (CA)

( * ) Notice: Subject to any disclaimer, the term of this patent is extended or adjusted under 35 U.S.C. 154(b) by 811 days.

(21) Appl. No.: 17/995,136

(22) PCT Filed: Mar. 29, 2021

(86) PCT No.: PCT/CA2021/050406
§ 371 (c)(1),
(2) Date: Sep. 30, 2022

(87) PCT Pub. No.: WO2021/195751
PCT Pub. Date: Oct. 7, 2021

(65) Prior Publication Data

US 2023/0105720 A1 Apr. 6, 2023

Related U.S. Application Data

(60) Provisional application No. 63/002,712, filed on Mar. 31, 2020.

(51) Int. Cl.
*C07C 37/48* (2006.01)
*C07C 309/65* (2006.01)

(52) U.S. Cl.
CPC ............ *C07C 37/48* (2013.01); *C07C 309/65* (2013.01)

(58) Field of Classification Search
CPC .. C07C 309/65; C07C 37/0555; C07C 309/66
USPC ........................................................... 562/42
See application file for complete search history.

(56) References Cited

FOREIGN PATENT DOCUMENTS

WO WO-2020232545 A1 11/2020
WO WO-2021195751 A1 10/2021

OTHER PUBLICATIONS

"International Application No. PCT/CA2021/050406, International Search Report and Written Opinion dated May 11, 2021", (May 11, 2021), 13 pgs.
Baek, Seung-Hwa, et al., "Synthesis and Antitumor Activity of Cannabigerol", Arch. Pharm. Res., vol. 19, No. 3, (1996), 228-230.
Cascio, M. G., et al., "Evidence that the plant cannabinoid cannabigerol is a highly potent alpha-2-adrenoceptor agonist and moderately potent 5HT1A receptor antagonist", British Journal of Pharmacology (2010), 159, 129-141, (Dec. 4, 2009), 129-141.
Singh, Mandeep, et al., "pPapaerlladium-Catalyzed Routes to Geranylated or Farnesylated Phenolic Stilbenes: Synthesis of Pawhuskin C and Schweinfurthin J", Synthesis 2012, 44, 2895-2902, (Aug. 8, 2012), 2895-2902.

*Primary Examiner* — Ana Z Muresan
(74) *Attorney, Agent, or Firm* — Schwegman Ludberg & Woessner, P.A.

(57) ABSTRACT

The present disclosure relates to cannabigerol sulfonate esters of formula (1).

6 Claims, 1 Drawing Sheet

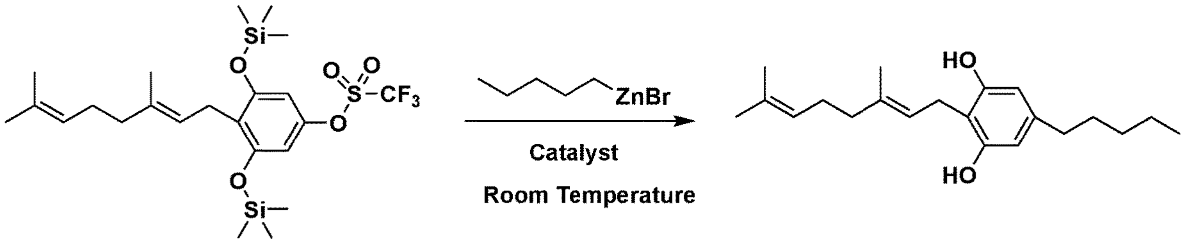
Catalyst
Room Temperature

CATALYTIC CANNABIGEROL PROCESSES AND PRECURSORS

CROSS-REFERENCE TO RELATED APPLICATIONS

This application is a U.S. national stage filing under 35 U.S.C. § 371 from International Application No. PCT/CA2021/050406, filed on 29 Mar. 2021, and published as WO2021/195751 on 7 Oct. 2021, which claims the benefit of priority to U.S. Provisional Application No. 63/002,712, filed Mar. 31, 2020, the benefit of priority of each of which is claimed herein, and which applications and publication are hereby incorporated herein by reference in their entirety.

FIELD OF THE DISCLOSURE

The present disclosure relates to cannabigerol sulfonate ester compounds and the use of the compounds for the preparation of cannabigerol and related compounds. The disclosure also relates to the use of catalysts and catalytic processes for the preparation of cannabigerol and related compounds using the cannabigerol sulfonate esters as precursors.

BACKGROUND OF THE DISCLOSURE

Cannabigerol (CBG) is a minor and non-psychoactive constituent of the *cannabis* plant. During growth, most of the CBG is converted into the other cannabinoids, including cannabidiol (CBD) and tetrahydrocannabinol (THC), and as such, constitutes only about 1% of the extracted cannabinoid content.

CBG is being investigated to determine its pharmacological properties and its potential pharmaceutical applications. CBG displays CB1 and CB2 binding affinity. It is being studied for the treatment of colitis, neuroinflammation, anxiety, depression and multiple sclerosis. It has been shown to reduce intra-ocular pressure in the eyes of glaucoma patients and to reduce bowel inflammation in mice. The latter was so effective that it was recommended for clinical investigations of IBD (M. G. Cascio et al. *British Journal of Pharmacology,* 2010, 159, 129-141). CBG is also being investigated for treating inflammation, arthritis, cancer, migraine, and neuropathic pain (M. G. Cascio et al. *British Journal of Pharmacology,* 2010, 159, 129-141).

As such, CBG potentially has significant medicinal benefits. It also counteracts the psychoactive effect of tetrahydrocannabinol (THC); one of the main component of *cannabis.*

The demand for pure CBG is growing rapidly and is complicated by its naturally low constituent in the *cannabis* plant. Hence, the best option is synthesis. The advantage of synthesized CBG relative to extracting the product from the *cannabis* plant is the stability of supply, and control over quality and scalability. The output can always be adjusted depending on demand.

Most of the synthetic approaches for CBG involve the acid catalyzed alkylation of olivetol with citral However, this procedure tends to give a mixture of products which have to be separated and purified using chromatography (S.-H. Baek et al. *Arch. Pharm. Res.* 1996, 19, 228-230).

The prior art reflects the difficulties associated with developing reliable and commercially viable routes for synthetic CBG. This is partly due to the nature of the reaction, which makes it difficult to separate pure CBG from its byproducts. The extremely low content and even undetectable amounts of the other related cannabigerol compounds in the *cannabis* plant, such as CBGV, CBGB and CBGP, means that synthesis is the only practical route to access these compounds. Hence, there is a need for a better process for developing synthetic CBG and related compounds.

SUMMARY OF THE DISCLOSURE

The present invention, in some aspects, describes an approach to developing synthetic CBG that focuses on the use of cheap and commercially available chemicals and use of these chemicals to prepare stable precursors that can be transformed into CBG and its analogues. These commercially available chemicals include, but are not limited to geraniol, citral, resorcinol and their derivatives.

In various aspects, the invention relates to the preparation of new cannabigerol sulfonate ester compounds and the use of such sulfonate ester compounds for the preparation of CBG and related products using catalysts and catalytic processes to substitute the sulfonate groups. The cannabigerol sulfonate esters can be prepared and purified prior to transformation to the desired individual cannabigerol products. The cannabigerol sulfonate esters are air-stable and shelf-stable compounds that can be stored, transported and converted into the desired cannabigerol products on demand.

Accordingly, in some embodiments, the present invention relates to cannabigerol sulfonate esters of Formula (I):

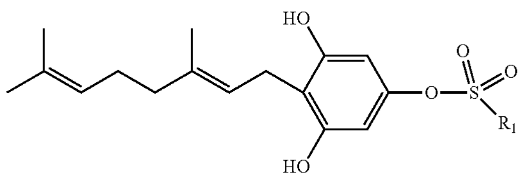

(I)

wherein, $R^1$ represents a hydrogen atom, a linear or branched alkyl group of any length, possibly substituted, or an alkenyl group of any length, possibly substituted, or an alkynyl group, possibly substituted, or a cycloalkyl group, possibly substituted, or an aryl group, possibly substituted, or an heteroaryl group, possibly substituted, or an $OR^c$ group or an $NR^c_2$ group, possibly substituted, with possible and non-limiting substituents of $R^1$ being halogen atoms, $OR^c$, or $NR^c_2$ groups, in which $R^c$ is a hydrogen atom or a cyclic, linear or branched alkyl, aryl or alkenyl group, and all stereoisomers thereof. In a general way, the compounds of Formula (I) can be prepared and isolated prior to use.

In certain embodiments, $R^1$ represents a hydrogen atom, an optionally substituted $C_1$-$C_{20}$(alkyl) group, an optionally substituted $C_2$-$C_{20}$(alkenyl) group, an optionally substituted $C_2$-$C_{20}$(alkynyl) group, an optionally substituted $C_3$-$C_{20}$ (cycloalkyl) group, an optionally substituted ($C_6$-$C_{14}$)-aryl group, an optionally substituted ($C_5$-$C_{14}$)-heteroaryl group, an $OR^c$ group or an $NR^c_2$ group, wherein $R^c$ is hydrogen, $C_1$-$C_{20}$(alkyl), $C_2$-$C_{20}$(alkenyl), $C_1$-$C_{20}$(alkynyl), $C_3$-$C_{20}$ (cycloalkyl) or ($C_6$-$C_{14}$)-aryl, and wherein the optional substituents on each of the above groups is halogen, $OR^d$ or $NR^c_2$.

In some other aspects, the present disclosure also relates to cannabinoid sulfonate esters of Formula (II):

(II)

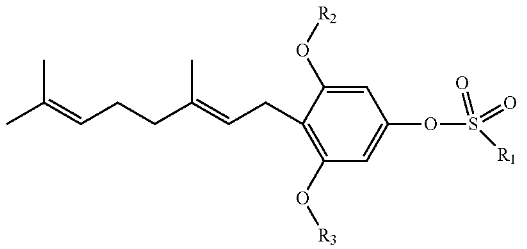

wherein, $R^1$ represents a hydrogen atom, a linear or branched alkyl group of any length, possibly substituted, or an alkenyl group of any length, possibly substituted, or an alkynyl group, possibly substituted, or a cycloalkyl group, possibly substituted, or an aryl group, possibly substituted, or an heteroaryl group, possibly substituted, or an $OR^c$ group or an $NR^c_2$ group, possibly substituted, with possible and non-limiting substituents of $R^1$ being halogen atoms, $OR^c$, or $NR^c_2$ groups, in which $R^c$ is a hydrogen atom or a cyclic, linear or branched alkyl, aryl or alkenyl group;

and $R_2$ and $R_3$ independently or simultaneously represent a linear or branched alkyl group of any length, possibly substituted, or an alkenyl group of any length, possibly substituted, or an alkynyl group, possibly substituted, or a cycloalkyl group, possibly substituted, or an aryl group, possibly substituted, or an heteroaryl group, possibly substituted, or an acyl group, possibly substituted, and one or more of the carbon atoms in the alkyl, alkenyl, alkynyl, cycloalkyl, aryl, heteroaryl or acyl groups of $R_2$ and/or $R_3$ is optionally replaced with a heteroatom selected from the group consisting of O, S, N, P and Si, which, where possible, is optionally substituted with one or more groups, and all stereoisomers thereof. In a general way, the compounds of Formula (II) can be prepared and isolated prior to use.

In certain embodiments, $R^1$ represents a hydrogen atom, an optionally substituted $C_1$-$C_{20}$(alkyl) group, an optionally substituted $C_2$-$C_{20}$(alkenyl) group, an optionally substituted $C_2$-$C_{20}$(alkynyl) group, an optionally substituted $C_3$-$C_{20}$ (cycloalkyl) group, an optionally substituted ($C_6$-$C_{14}$)-aryl group, an optionally substituted ($C_5$-$C_{14}$)-heteroaryl group, an $OR^c$ group or an $NR^c_2$ group, wherein $R^c$ is hydrogen, $C_1$-$C_{20}$(alkyl), $C_2$-$C_{20}$(alkenyl), $C_1$-$C_{20}$(alkynyl), $C_3$-$C_{20}$ (cycloalkyl) or ($C_6$-$C_{14}$)-aryl, and wherein the optional substituents on each of the above groups is halogen, $OR^d$ or $NR^c_2$.

In further embodiments, $R_2$ and $R_3$ independently or simultaneously represent an optionally substituted $C_1$-$C_{20}$ (alkyl) group, an optionally substituted $C_2$-$C_{20}$(alkenyl) group, an optionally substituted $C_2$-$C_{20}$(alkynyl) group, an optionally substituted $C_3$-$C_{20}$(cycloalkyl) group, an optionally substituted ($C_6$-$C_{14}$)-aryl group, or an optionally substituted acyl group —C(=O)—($C_1$-$C_{20}$)-alkyl, wherein one or more of the carbon atoms in the alkyl, alkenyl, alkynyl, cycloalkyl, aryl, heteroaryl or acyl groups of $R_2$ and/or $R_3$ is optionally replaced with a heteroatom selected from the group consisting of O, S, N, P and Si, which, where possible, is optionally substituted with one or more groups which are $C_1$-$C_{20}$(alkyl) group, $C_2$-$C_{20}$(alkenyl) group, $C_2$-$C_{20}$(alkynyl) group, $C_3$-$C_{20}$(cycloalkyl) group, or ($C_6$-$C_{14}$)-aryl group.

In various embodiments of the invention, the transformations to which the compounds of the invention can be applied include but are not limited to catalytic and non-catalytic carbon-carbon bond forming reactions including Ullman, Suzuki-Miyaura, Negishi, Kumada, Sonogashira and Stille reactions. Such carbon-carbon bond forming reactions include the use of compounds of the present disclosure, such as those of Formula (I) and (II) to prepare one or more of the cannabigerol compounds selected from the group consisting of:

Formula (III):

(III)

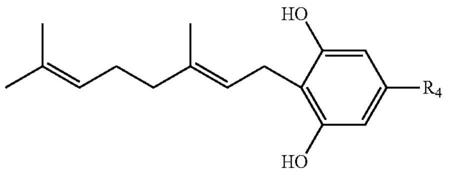

and Formula (IV):

(IV)

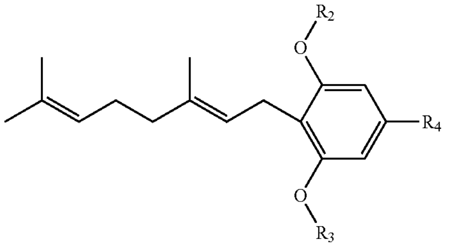

wherein, $R_2$ and $R_3$ independently or simultaneously represent a linear or branched alkyl group of any length, possibly substituted, or an alkenyl group of any length, possibly substituted, or an alkynyl group, possibly substituted, or a cycloalkyl group, possibly substituted, or an aryl group, possibly substituted, or an heteroaryl group, possibly substituted, or an acyl group, possibly substituted, and one or more of the carbon atoms in the alkyl, alkenyl, alkynyl, cycloalkyl, aryl, heteroaryl or acyl groups of $R_2$ and/or $R_3$ is optionally replaced with a heteroatom selected from the group consisting of O, S, N, P and Si, which, where possible, is optionally substituted with one or more groups; and $R_4$ represents a hydrogen atom, a linear or branched alkyl group of any length, possibly substituted, or an alkenyl group of any length, possibly substituted, or an alkynyl group, possibly substituted, or a cycloalkyl group, possibly substituted, or an aryl group, possibly substituted, and all stereoisomers thereof.

In further embodiments, $R_2$ and $R_3$ independently or simultaneously represent an optionally substituted $C_1$-$C_{20}$ (alkyl) group, an optionally substituted $C_2$-$C_{20}$(alkenyl) group, an optionally substituted $C_2$-$C_{20}$(alkynyl) group, an optionally substituted $C_3$-$C_{20}$(cycloalkyl) group, an optionally substituted ($C_6$-$C_{14}$)-aryl group, or an optionally substituted acyl group —C(=O)—($C_1$-$C_{20}$)-alkyl, wherein one or more of the carbon atoms in the alkyl, alkenyl, alkynyl, cycloalkyl, aryl, heteroaryl or acyl groups of $R_2$ and/or $R_3$ is optionally replaced with a heteroatom selected from the group consisting of O, S, N, P and Si, which, where possible, is optionally substituted with one or more groups which are $C_1$-$C_{20}$(alkyl) group, $C_2$-$C_{20}$(alkenyl) group, $C_2$-$C_{20}$(alkynyl) group, $C_3$-$C_{20}$(cycloalkyl) group, or ($C_6$-$C_{14}$)-aryl group.

In another embodiment, $R_4$ represents a hydrogen atom, an optionally substituted $C_1$-$C_{20}$(alkyl) group, an optionally substituted $C_2$-$C_{20}$(alkenyl) group, an optionally substituted $C_2$-$C_{20}$(alkynyl) group, an optionally substituted $C_3$-$C_{20}$ (cycloalkyl) group, or an optionally substituted ($C_6$-$C_{14}$)-aryl group, wherein the optional substituents are a $C_1$-$C_{20}$ (alkyl) group, a $C_2$-$C_{20}$(alkenyl) group, a $C_2$-$C_{20}$(alkynyl) group, a $C_3$-$C_{20}$(cycloalkyl) group, or a ($C_6$-$C_{14}$)-aryl group.

In some other aspects of the invention, the present invention provides a method for the synthesis of one or more of the cannabigerol products below:

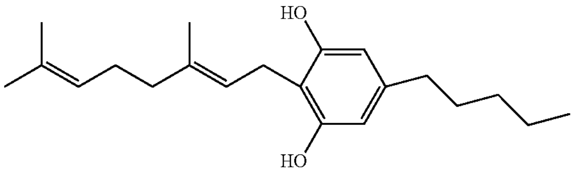

Cannabigerol
CBG

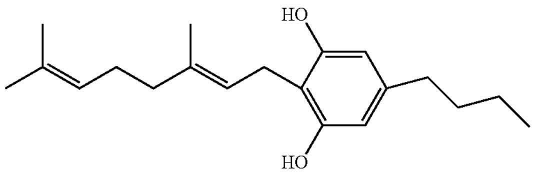

Cannabigerolbutol
CBGB

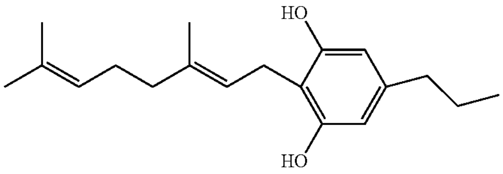

Cannabigerovarin
CBGV

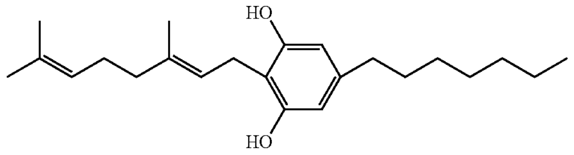

Cannabigerophorbol
CBGP

In some aspects the invention provides a process for the catalytic preparation of a compound of Formula (III) or Formula (IV) from a compound of Formula (I) or Formula (II). In some other aspects the invention provides a process for the non-catalytic preparation of a compound of Formula (III) or Formula (IV) from a compound of Formula (I) or Formula (II). In various embodiments, the process for the preparation of a compound of Formula (III) or Formula (IV) from a compound of Formula (I) or Formula (II) pursuant to the invention uses a boron containing compound such as $R_4$—$B(OH)_2$, $R_4$—$B(OR)_2$ or $R_4$—$BF_3K$, wherein $R_4$ represents a hydrogen atom, an optionally substituted $C_1$-$C_{20}$ (alkyl) group, an optionally substituted $C_2$-$C_{20}$(alkenyl) group, an optionally substituted $C_2$-$C_{20}$(alkynyl) group, an optionally substituted $C_3$-$C_{20}$(cycloalkyl) group, or an optionally substituted ($C_6$-$C_{14}$)-aryl group, wherein the optional substituents are a $C_1$-$C_{20}$(alkyl) group, a $C_2$-$C_{20}$ (alkenyl) group, a $C_2$-$C_{20}$(alkynyl) group, a $C_3$-$C_{20}$(cycloalkyl) group, or a ($C_6$-$C_{14}$)-aryl group. In some other aspects of the process of the invention a Grignard compound such as $R_4$—MgX is used to prepare Formula (III) or Formula (IV). In still other aspects of the process of the invention an organozinc compound such as $R_4$—ZnX is used to prepare Formula (III) or Formula (IV), wherein X is halo.

In some aspects, the invention provides a compound or composition comprising: Formula (III) or Formula (VI) where the compounds, or compositions as the case may be, are a mixture of isomers.

In some other aspects, the compounds and compositions of the invention comprise all isomers of compounds of Formula (I) and Formula (II). In some other embodiments it provides a mixture of isomers of compounds of Formula (I) and Formula (II). In yet some other embodiment it provides single isomers of compounds of Formula (I) and Formula (II). In some other aspects, the invention provides processes and methods for producing any of the foregoing.

The present invention also includes, compositions, methods of producing the compound and compositions comprising the compounds of the invention, kits comprising any one or more of the components of the foregoing, optionally with instructions to make or use same and uses of any of the foregoing.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

The invention will be described in greater detail with reference to the following drawings, which are meant to be illustrative by certain embodiments of the invention and are not meant to limit the scope of the invention:

FIG. 1 shows the Scheme for the preparation of CBG using (E)-4-(3,7-dimethylocta-2,6-dienyl)-3,5-bis(trimethylsilyloxy)phenyl trifluoromethanesulfonate.

DETAILED DESCRIPTION OF THE DISCLOSURE

(I) Definitions

The term "alkyl" as used herein means straight and/or branched chain, saturated alkyl radicals containing one or more carbon atoms having the formula $C_n$-$C_m$ and includes (depending on the identity of n and m) methyl, ethyl, propyl, isopropyl, n-butyl, s-butyl, isobutyl, t-butyl, 2,2-dimethylbutyl, n-pentyl, 2-methylpentyl, 3-methylpentyl, 4-methylpentyl, n-hexyl and the like.

The term "alkenyl" as used herein means straight and/or branched chain, unsaturated alkyl radicals containing two or more carbon atoms and one to three double bonds having the formula $C_n$-$C_m$, and includes (depending on the identity of n and m) vinyl, allyl, 2-methylprop-1-enyl, but-1-enyl, but-2-enyl, but-3-enyl, 2-methylbut-1-enyl, 2-methylpent-1-enyl, 4-methylpent-1-enyl, 4-methylpent-2-enyl, 2-methylpent-2-enyl, 4-methylpenta-1,3-dienyl, hexen-1-yl and the like.

The term "alkynyl" as used herein means straight and/or branched chain, unsaturated alkyl radicals containing two or more carbon atoms and one to three triple bonds having the formula $C_n$-$C_m$, and includes (depending on the identity n and m) acetylynyl, propynyl, but-1-ynyl, but-2-ynyl, but-3-ynyl, 3-methylbut-1-enyl, 3-methylpent-1-ynyl, 4-methyl-pent-1-ynyl, 4-methylpent-2-ynyl, penta-1,3-di-ynyl, hexyn-1-yl and the like.

The term "alkoxy" as used herein means straight and/or branched chain alkoxy group containing one or more carbon atoms having the formula $C_n$-$C_m$ and includes (depending on the identity n and m) methoxy, ethoxy, propyloxy, isopropyloxy, t-butoxy, heptoxy, and the like.

The term "cycloalkyl" as used herein means a monocyclic, bicyclic or tricyclic saturated carbocylic group containing three or more carbon atoms having the formula $C_n$-$C_m$ and includes (depending on the identity n and m) cyclopropyl, cyclobutyl, cyclopentyl, cyclodecyl and the like.

The term "aryl" as used herein means a monocyclic, bicyclic or tricyclic aromatic ring system containing at least one aromatic ring and 6 or more carbon atoms and includes phenyl, naphthyl, anthracenyl, 1,2-dihydronaphthyl, 1,2,3,4-tetrahydronaphthyl, fluorenyl, indanyl, indenyl and the like.

The term "heteroaryl" as used herein means a monocyclic, bicyclic or tricyclic ring system containing one or two aromatic rings and 5 or more atoms of which, unless otherwise specified, one, two, three, four or five are heteromoieties independently selected from N, NH, N(alkyl), O and S and includes thienyl, furyl, pyrrolyl, pyrididyl, indolyl, quinolyl, isoquinolyl, tetrahydroquinolyl, benzofuryl, benzothienyl and the like.

The term "halo" as used herein means halogen and includes chloro, fluoro, bromo or iodo.

The term "fluoro-substituted" as used herein means that at least one, including all, of the hydrogens on the referenced group is replaced with fluorine.

The suffix "ene" added on to any of the above groups means that the group is divalent, i.e. inserted between two other groups.

The term "ring system" as used herein refers to a carbon-containing ring system, that includes monocycles, fused bicyclic and polycyclic rings, bridged rings and metallocenes. Where specified, the carbons in the rings may be substituted or replaced with heteroatoms.

The term "leaving group" as used herein refers to a substituent that is present on a chemical compound and can be displaced. The particular leaving group utilized is dependent upon the specific reaction being performed and can readily be determined by one of skill in the art.

The term "stereoisomers" as used herein refers to all geometric isomers, enantiomers or diastereomers. These compounds may be designated by the symbols "E," "Z," "R" or "S," depending on the configuration of substituents around the stereogenic carbon atoms. The present disclosure encompasses various stereoisomers of these compounds and mixtures thereof. Stereoisomers include enantiomers, diastereomers and double bond isomers.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. For instance, "including" also encompasses "including but not limited to". Finally, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

(II) Compounds of the Disclosure

The present disclosure relates to cannabigerol sulfonate esters of Formula (I):

(I)

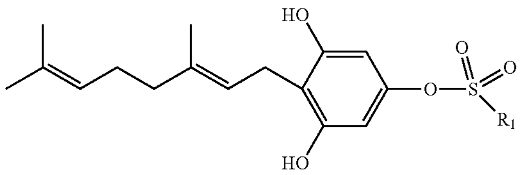

wherein, $R_1$ represents a hydrogen atom, a linear or branched alkyl group of any length, possibly substituted, or an alkenyl group of any length, possibly substituted, or an alkynyl group, possibly substituted, or a cycloalkyl group, possibly substituted, or an aryl group, possibly substituted, or an heteroaryl group, possibly substituted, or an $OR^c$ group or an $NR^c_2$ group, possibly substituted, with possible and non-limiting substituents of $R_1$ being halogen atoms, $OR^c$, or $NR^c_2$ groups, in which $R^c$ is a hydrogen atom or a cyclic, linear or branched alkyl, aryl or alkenyl group. In a general way, the compounds of Formula (I) can be prepared and isolated prior to use.

In certain embodiments, $R^1$ represents a hydrogen atom, an optionally substituted $C_1$-$C_{20}$(alkyl) group, an optionally substituted $C_2$-$C_{20}$(alkenyl) group, an optionally substituted $C_2$-$C_{20}$(alkynyl) group, an optionally substituted $C_3$-$C_{20}$ (cycloalkyl) group, an optionally substituted ($C_6$-$C_{14}$)-aryl group, an optionally substituted ($C_5$-$C_{14}$)-heteroaryl group, an $OR^c$ group or an $NR^c_2$ group, wherein $R^c$ is hydrogen, $C_1$-$C_{20}$(alkyl), $C_2$-$C_{20}$(alkenyl), $C_1$-$C_{20}$(alkynyl), $C_3$-$C_{20}$ (cycloalkyl) or ($C_6$-$C_{14}$)-aryl, and wherein the optional substituents on each of the above groups is halogen, $OR^d$ or $NR^d_2$.

In another embodiment, $R^1$ represents a hydrogen atom, an optionally substituted $C_1$-$C_{10}$(alkyl) group, an optionally substituted $C_2$-$C_{10}$(alkenyl) group, an optionally substituted $C_2$-$C_{10}$(alkynyl) group, an optionally substituted $C_3$-$C_{10}$ (cycloalkyl) group, an optionally substituted ($C_6$-$C_{10}$)-aryl group, an optionally substituted ($C_5$-$C_{10}$)-heteroaryl group, an $OR^c$ group or an $NR^c_2$ group.

In another embodiment, $R^1$ represents a hydrogen atom, an optionally substituted $C_1$-$C_6$(alkyl) group, an optionally substituted $C_2$-$C_6$(alkenyl) group, an optionally substituted $C_2$-$C_6$(alkynyl) group, an optionally substituted $C_3$-$C_6$(cycloalkyl) group, an optionally substituted ($C_6$)-aryl group, an optionally substituted ($C_5$-$C_6$)-heteroaryl group, an $OR^c$ group or an $NR^c_2$ group.

In another embodiment, $R^1$ represents a hydrogen atom, an optionally substituted $C_1$-$C_6$(alkyl) group.

In another embodiment, $R^1$ represents an optionally substituted $C_1$-$C_6$(alkyl) group. In another embodiment, $R^1$ represents a halo-substituted $C_1$-$C_6$(alkyl) group. In another embodiment, $R^1$ represents $CF_3$.

In another embodiment, $R^c$ is hydrogen, $C_1$-$C_{10}$(alkyl), $C_2$-$C_{10}$(alkenyl), $C_1$-$C_{10}$(alkynyl), $C_3$-$C_{10}$(cycloalkyl) or ($C_6$-$C_{10}$)-aryl. In another embodiment, $R^c$ is hydrogen, $C_1$-$C_6$(alkyl), $C_2$-$C_6$(alkenyl), $C_1$-$C_6$(alkynyl), $C_3$-$C_6$(cycloalkyl) or ($C_6$)-aryl.

In another embodiment, the optional substituents on each of the groups defined by $R^1$ is halogen, $OR^d$ or $NR^d_2$. In one embodiment, halogen is F.

In one embodiment, the compound of Formula (I) is

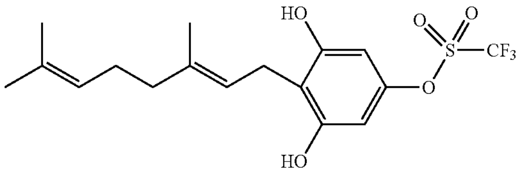 [SMILES: CC(C)=CCC/C(C)=C/Cc1c(O)cc(OS(=O)(=O)C(F)(F)F)cc1O]

The present disclosure also relates to cannabigerol derivatives having a leaving group (LG) which allows for the facile preparation of compounds of the Formula (III). In one embodiment, the cannabigerol derivatives having a leaving group (LG) have the Formula (A):

Formula (A)

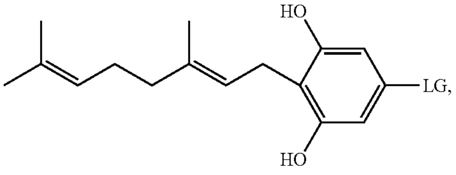

wherein LG is a suitable leaving group.

In another embodiment, the suitable leaving group is:

(i) an anionic (anionic after leaving) group such as sulphonates, halides or boronates;

(ii) $MX_n$ groups (M=B, Si; X is halide, OH, OR, ($C_1$-$C_{20}$)-alkyl, ($C_1$-$C_{20}$)-aryl, etc.; n=2 to 3).

In another embodiment, the boronate leaving group is —$B(OR)_2$, where R is H, a ($C_1$-$C_{20}$)-alkyl group, a ($C_2$-$C_{20}$)-alkenyl group, a ($C_2$-$C_{20}$)-alkynyl group, a ($C_3$-$C_{20}$)-cycloalkyl group, or a ($C_6$-$C_{14}$)-aryl group. In another embodiment, the boronate leaving group is —$B(OR)_2$, where R is H, a ($C_1$-$C_{20}$)-alkyl group (such as a ($C_1$-$C_{10}$)-alkyl group) or a ($C_6$-$C_{14}$)-aryl group (such as a ($C_6$-$C_{10}$)-aryl group). In another embodiment, the boronate leaving group is —$BF_3K$.

The present disclosure also relates to cannabigerol sulfonate esters of Formula (II):

(II)

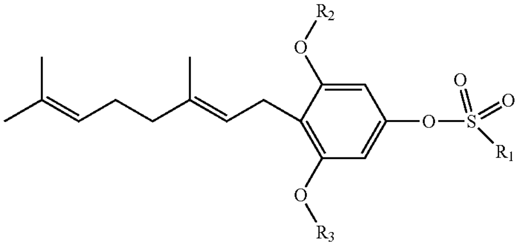

wherein, $R^1$ represents a hydrogen atom, a linear or branched alkyl group of any length, possibly substituted, or an alkenyl group of any length, possibly substituted, or an alkynyl group, possibly substituted, or a cycloalkyl group, possibly substituted, or an aryl group, possibly substituted, or an heteroaryl group, possibly substituted, or an $OR^c$ group or an $NR^c_2$ group, possibly substituted, with possible and non-limiting substituents of $R^1$ being halogen atoms, $OR^c$, or $NR^c_2$ groups, in which $R^c$ is a hydrogen atom or a cyclic, linear or branched alkyl, aryl or alkenyl group;

and $R_2$ and $R_3$ independently or simultaneously represent a linear or branched alkyl group of any length, possibly substituted, or an alkenyl group of any length, possibly substituted, or an alkynyl group, possibly substituted, or a cycloalkyl group, possibly substituted, or an aryl group, possibly substituted, or an heteroaryl group, possibly substituted, or an acyl group, possibly substituted, and one or more of the carbon atoms in the alkyl, alkenyl, alkynyl, cycloalkyl, aryl, heteroaryl or acyl groups of $R_2$ and/or $R_3$ is optionally replaced with a heteroatom selected from the group consisting of O, S, N, P and Si, which, where possible, is optionally substituted with one or more groups. In a general way, the compounds of Formula (II) can be prepared and isolated prior to use.

In certain embodiments, $R^1$ represents a hydrogen atom, an optionally substituted $C_1$-$C_{20}$(alkyl) group, an optionally substituted $C_2$-$C_{20}$(alkenyl) group, an optionally substituted $C_2$-$C_{20}$(alkynyl) group, an optionally substituted $C_3$-$C_{20}$(cycloalkyl) group, an optionally substituted ($C_6$-$C_{14}$)-aryl group, an optionally substituted ($C_5$-$C_{14}$)-heteroaryl group, an OW group or an $NR^c_2$ group, wherein $R^c$ is hydrogen, $C_1$-$C_{20}$(alkyl), $C_2$-$C_{20}$(alkenyl), $C_1$-$C_{20}$(alkynyl), $C_3$-$C_{20}$(cycloalkyl) or ($C_6$-$C_{14}$)-aryl, and wherein the optional substituents on each of the above groups is halogen, $OR^d$ or $NR^c_2$.

In another embodiment, $R^1$ represents a hydrogen atom, an optionally substituted $C_1$-$C_{10}$(alkyl) group, an optionally substituted $C_2$-$C_{10}$(alkenyl) group, an optionally substituted $C_2$-$C_{10}$(alkynyl) group, an optionally substituted $C_3$-$C_{10}$(cycloalkyl) group, an optionally substituted ($C_6$-$C_{10}$)-aryl group, an optionally substituted ($C_5$-$C_{10}$)-heteroaryl group, an OW group or an $NR^c_2$ group.

In another embodiment, $R^1$ represents a hydrogen atom, an optionally substituted $C_1$-$C_6$(alkyl) group, an optionally substituted $C_2$-$C_6$(alkenyl) group, an optionally substituted $C_2$-$C_6$(alkynyl) group, an optionally substituted $C_3$-$C_6$(cycloalkyl) group, an optionally substituted ($C_6$)-aryl group, an optionally substituted ($C_5$-$C_6$)-heteroaryl group, an OW group or an $NR^c_2$ group.

In another embodiment, $R^1$ represents a hydrogen atom, an optionally substituted $C_1$-$C_6$(alkyl) group.

In another embodiment, $R^1$ represents an optionally substituted $C_1$-$C_6$(alkyl) group. In another embodiment, $R^1$ represents a halo-substituted $C_1$-$C_6$(alkyl) group. In another embodiment, $R^1$ represents $CF_3$.

In another embodiment, $R^c$ is hydrogen, $C_1$-$C_{10}$(alkyl), $C_2$-$C_{10}$(alkenyl), $C_1$-$C_{10}$(alkynyl), $C_3$-$C_{10}$(cycloalkyl) or ($C_6$-$C_{10}$)-aryl. In another embodiment, $R^c$ is hydrogen, $C_1$-$C_6$(alkyl), $C_2$-$C_6$(alkenyl), $C_1$-$C_6$(alkynyl), $C_3$-$C_6$(cycloalkyl) or ($C_6$)-aryl.

In another embodiment, the optional substituents on each of the groups defined by $R^1$ is halogen, $OR^d$ or $NR^d_2$. In one embodiment, halogen is F.

In further embodiments, $R_2$ and $R_3$ independently or simultaneously represent an optionally substituted $C_1$-$C_{20}$(alkyl) group, an optionally substituted $C_2$-$C_{20}$(alkenyl) group, an optionally substituted $C_2$-$C_{20}$(alkynyl) group, an optionally substituted $C_3$-$C_{20}$(cycloalkyl) group, an optionally substituted ($C_6$-$C_{14}$)-aryl group, or an optionally substituted acyl group —C(═O)—($C_1$-$C_{20}$)-alkyl.

In further embodiments, $R_2$ and $R_3$ independently or simultaneously represent an optionally substituted $C_1$-$C_{10}$ (alkyl) group, an optionally substituted $C_2$-$C_{10}$(alkenyl) group, an optionally substituted $C_2$-$C_{10}$(alkynyl) group, an optionally substituted $C_3$-$C_{10}$(cycloalkyl) group, an optionally substituted ($C_6$-$C_{10}$)-aryl group, or an optionally substituted acyl group —C(═O)—($C_1$-$C_{10}$)-alkyl.

In further embodiments, $R_2$ and $R_3$ independently or simultaneously represent an optionally substituted $C_1$-$C_6$ (alkyl) group, an optionally substituted $C_2$-$C_6$(alkenyl) group, an optionally substituted $C_2$-$C_6$(alkynyl) group, an optionally substituted $C_3$-$C_6$(cycloalkyl) group, an optionally substituted ($C_6$)-aryl group, or an optionally substituted acyl group —C(═O)—($C_1$-$C_6$)-alkyl.

In further embodiments, $R_2$ and $R_3$ independently or simultaneously represent an optionally substituted $C_1$-$C_6$ (alkyl) group, an optionally substituted $C_2$-$C_6$(alkenyl) group, an optionally substituted $C_2$-$C_6$(alkynyl) group, an optionally substituted $C_3$-$C_6$(cycloalkyl) group, an optionally substituted ($C_6$)-aryl group, or an optionally substituted acyl group —C(═O)—($C_1$-$C_6$)-alkyl.

In one embodiment, one or more of the carbon atoms in the alkyl, alkenyl, alkynyl, cycloalkyl, aryl, heteroaryl or acyl groups of $R_2$ and/or $R_3$ is optionally replaced with a heteroatom selected from the group consisting of O, S, N, P and Si, which, where possible, the heteroatom is optionally substituted with one or more groups, such as $C_1$-$C_6$(alkyl) group.

In another embodiment, $R_2$ and $R_3$ independently or simultaneously represent an optionally substituted $C_1$-$C_6$ (alkyl) group, wherein one carbon atom is replaced with a Si atom, substituted with one or more $C_1$-$C_6$(alkyl) groups. In another embodiment, $R_2$ and $R_3$ independently or simultaneously represent a —$CH_3$ group or a —$Si(CH_3)_3$ group.

In another embodiment, the compound of Formula (II) is

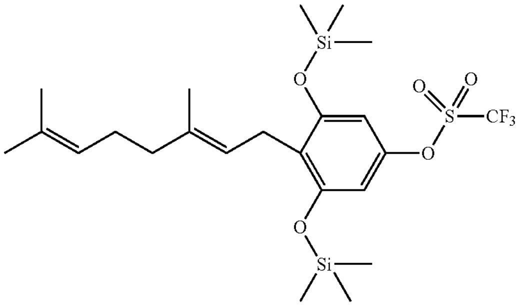

or

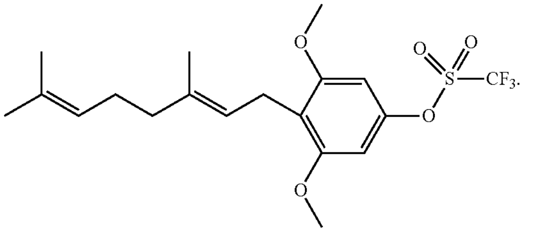

The present disclosure also relates to cannabigerol derivatives having a leaving group (LG) which allows for the facile preparation of compounds of the Formula (IV). In one embodiment, the cannabigerol derivatives having a leaving group (LG) have the Formula (B):

Formula (B)

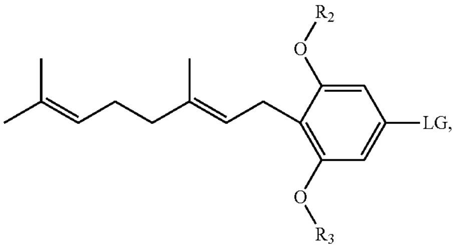

wherein LG is a suitable leaving group.

In another embodiment, the suitable leaving group is:

(i) an anionic (anionic after leaving) group such as sulphonates, halides or boronates;

(ii) $MX_n$ groups (M=Li, Mg, Zn, Sn, B, Si; X is halide, OH, OR, ($C_1$-$C_{20}$)-alkyl, ($C_1$-$C_{20}$)-aryl, etc.; n=0 to 3).

In another embodiment, the boronate leaving group is —$B(OR)_2$, where R is H, a ($C_1$-$C_{20}$)-alkyl group, a ($C_2$-$C_{20}$)-alkenyl group, a ($C_2$-$C_{20}$)-alkynyl group, a ($C_3$-$C_{20}$)-cycloalkyl group, or a ($C_6$-$C_{14}$)-aryl group. In another embodiment, the boronate leaving group is —$B(OR)_2$, where R is H, a ($C_1$-$C_{20}$)-alkyl group (such as a ($C_1$-$C_{10}$)-alkyl group) or a ($C_6$-$C_{14}$)-aryl group (such as a ($C_6$-$C_{10}$)-aryl group). In another embodiment, the boronate leaving group is —$BF_3K$.

The transformations to which the compounds of the disclosure can be applied include but are not limited to catalytic and non-catalytic carbon-carbon bond forming reactions including Ullman, Suzuki-Miyaura, Negishi, Kumada, Sonogashira and Stille reactions. Such carbon-carbon bond forming reactions include the use of compounds of the disclosure to prepare cannabigerol compounds of Formula (III):

(III)

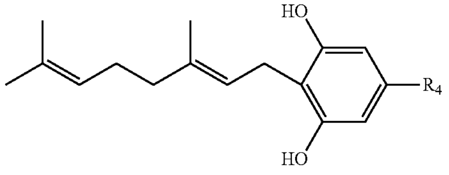

and Formula (IV):

(IV)

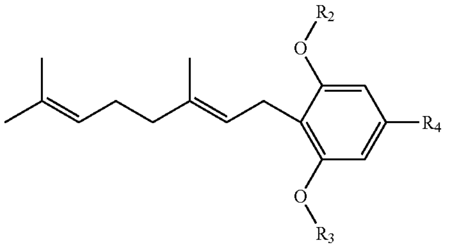

wherein, $R_2$ and $R_3$ represents a linear or branched alkyl group of any length, possibly substituted, or an alkenyl group of any length, possibly substituted, or an alkynyl group, possibly substituted, or a cycloalkyl group, possibly substituted, or an aryl group, possibly substituted, or an heteroaryl group, possibly substituted, or an acyl group, possibly substituted, and one or more of the carbon atoms in the alkyl, alkenyl, alkynyl, cycloalkyl, aryl, heteroaryl or acyl groups of $R_2$ and/or $R_3$ is optionally replaced with a heteroatom selected from the group consisting of O, S, N, P and Si, which, where possible, is optionally substituted with one or more groups; and $R_4$ represents a hydrogen atom, a linear or branched alkyl group of any length, possibly substituted, or an alkenyl group of any length, possibly substituted, or an alkynyl group, possibly substituted, or a cycloalkyl group, possibly substituted, or an aryl group, possibly substituted.

In further embodiments, $R_2$ and $R_3$ independently or simultaneously represent an optionally substituted $C_1$-$C_{20}$ (alkyl) group, an optionally substituted $C_2$-$C_{20}$(alkenyl) group, an optionally substituted $C_2$-$C_{20}$(alkynyl) group, an optionally substituted $C_3$-$C_{20}$(cycloalkyl) group, an optionally substituted ($C_6$-$C_{14}$)-aryl group, or an optionally substituted acyl group —C(═O)—($C_1$-$C_{20}$)-alkyl.

In further embodiments, $R_2$ and $R_3$ independently or simultaneously represent an optionally substituted $C_1$-$C_{10}$ (alkyl) group, an optionally substituted $C_2$-$C_{10}$(alkenyl) group, an optionally substituted $C_2$-$C_{10}$(alkynyl) group, an optionally substituted $C_3$-$C_{10}$(cycloalkyl) group, an optionally substituted ($C_6$-$C_{10}$)-aryl group, or an optionally substituted acyl group —C(═O)—($C_1$-$C_{10}$)-alkyl.

In further embodiments, $R_2$ and $R_3$ independently or simultaneously represent an optionally substituted $C_1$-$C_6$ (alkyl) group, an optionally substituted $C_2$-$C_6$(alkenyl) group, an optionally substituted $C_2$-$C_6$(alkynyl) group, an optionally substituted $C_3$-$C_6$(cycloalkyl) group, an optionally substituted ($C_6$)-aryl group, or an optionally substituted acyl group —C(═O)—($C_1$-$C_6$)-alkyl.

In further embodiments, $R_2$ and $R_3$ independently or simultaneously represent an optionally substituted $C_1$-$C_6$ (alkyl) group, an optionally substituted $C_2$-$C_6$(alkenyl) group, an optionally substituted $C_2$-$C_6$(alkynyl) group, an optionally substituted $C_3$-$C_6$(cycloalkyl) group, an optionally substituted ($C_6$)-aryl group, or an optionally substituted acyl group —C(═O)—($C_1$-$C_6$)-alkyl.

In one embodiment, one or more of the carbon atoms in the alkyl, alkenyl, alkynyl, cycloalkyl, aryl, heteroaryl or acyl groups of $R_2$ and/or $R_3$ is optionally replaced with a heteroatom selected from the group consisting of O, S, N, P and Si, which, where possible, the heteroatom is optionally substituted with one or more groups, such as $C_1$-$C_6$(alkyl) group.

In another embodiment, $R_2$ and $R_3$ independently or simultaneously represent an optionally substituted $C_1$-$C_6$ (alkyl) group, wherein one carbon atom is replaced with a Si atom, substituted with one or more $C_1$-$C_6$(alkyl) groups. In another embodiment, $R_2$ and $R_3$ independently or simultaneously represent a —$CH_3$ group or a —$Si(CH_3)_3$ group.

In another embodiment, $R_4$ represents a hydrogen atom, an optionally substituted $C_1$-$C_{20}$(alkyl) group, an optionally substituted $C_2$-$C_{20}$(alkenyl) group, an optionally substituted $C_2$-$C_{20}$(alkynyl) group, an optionally substituted $C_3$-$C_{20}$ (cycloalkyl) group, or an optionally substituted ($C_6$-$C_{14}$)-aryl group, wherein the optional substituents are a $C_1$-$C_{20}$ (alkyl) group, a $C_2$-$C_{20}$(alkenyl) group, a $C_2$-$C_{20}$(alkynyl) group, a $C_3$-$C_{20}$(cycloalkyl) group, or a ($C_6$-$C_{14}$)-aryl group.

In another embodiment, $R_4$ represents a hydrogen atom, an optionally substituted $C_1$-$C_{10}$(alkyl) group, an optionally substituted $C_2$-$C_{10}$(alkenyl) group, an optionally substituted $C_2$-$C_{10}$(alkynyl) group, an optionally substituted $C_3$-$C_{10}$ (cycloalkyl) group, or an optionally substituted ($C_6$-$C_{10}$)-aryl group.

In another embodiment, $R_4$ represents a hydrogen atom, an optionally substituted $C_1$-$C_6$(alkyl) group, an optionally substituted $C_2$-$C_6$(alkenyl) group, an optionally substituted $C_2$-$C_6$(alkynyl) group, an optionally substituted $C_3$-$C_6$(cycloalkyl) group, or an optionally substituted ($C_6$)-aryl group.

In another embodiment, $R_4$ represents a hydrogen atom, an optionally substituted $C_1$-$C_7$(alkyl) group, substituted with an optionally substituted phenyl group.

In another embodiment, the compound of Formula (III) is

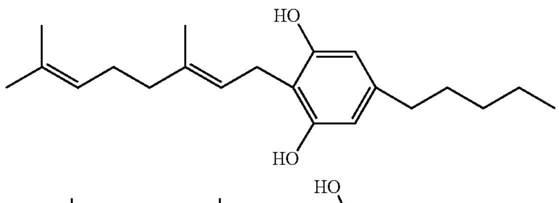
,
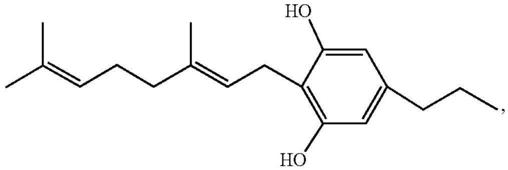
,
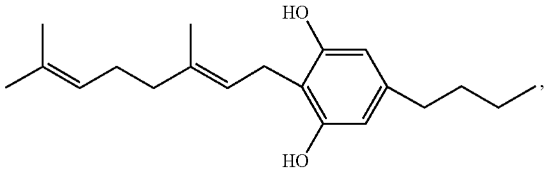
,
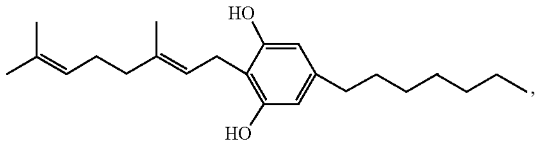
, or
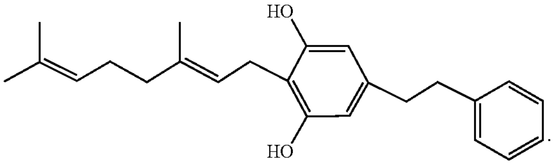
.

In another embodiment, the compound of Formula (IV) is

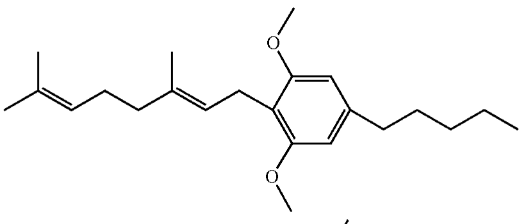
, or
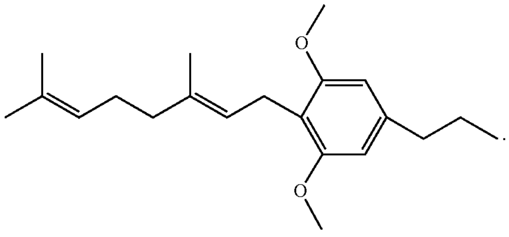
.

(III) Processes of the Disclosure

The present disclosure also relates to a process for the production of compounds of Formula (I) comprising first contacting a compound of Formula (V)

(V)

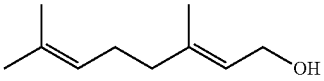

and a compound of Formula (VI), (VI)

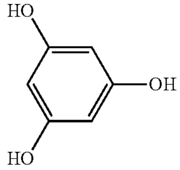

to form a compound of Formula (VII).

(VII)

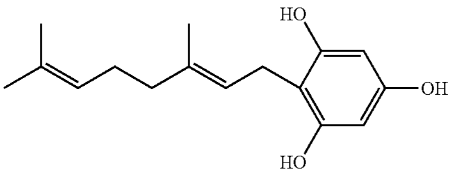

Compound (VII) is then transformed to a compound of Formula (I) or (A) by contacting a compound of Formula (VII) with the required sulfonylating reagent in the presence of a base (such as triethylamine, or an organic or inorganic base), or with the required leaving group reactant.

Compound (I) is then transformed to a compound of Formula (II) by contacting a compound of Formula (I) with a suitable reagent (such as methyl iodide, trimethylsilyl chloride) in the presence of a base (such as triethylamine, or an organic or inorganic base).

In some aspects, the transformation of Compound (V) and Compound (VI) to Compound (VII) requires a suitable acid catalyst. Suitable acid catalysts include but are not limited to Lewis acids, organic acids and inorganic acids (such as $BF_3.Et_2O$, $AlCl_3$, $ZnBr_2$, $ZnCl_2$, $HBF_4$, oxalic acid, acetic acid, formic acid).

The disclosure also relates to a process for the catalytic and non-catalytic use of compounds of Formula (I) or (A) and Formula (II) or (B) to prepare cannabigerol compounds of Formula (III):

(III)

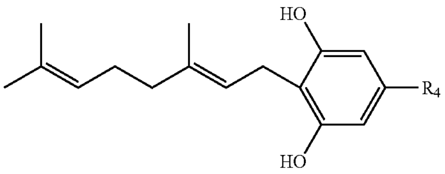

and Formula (IV):

(IV)

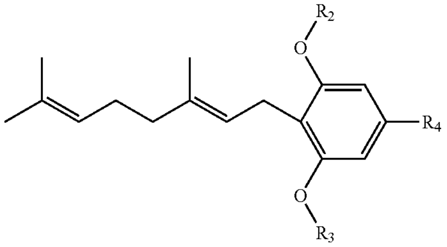

wherein, $R_2$ and $R_3$ represents a linear or branched alkyl group of any length, possibly substituted, or an alkenyl group of any length, possibly substituted, or an alkynyl group, possibly substituted, or a cycloalkyl group, possibly substituted, or an aryl group, possibly substituted, or an heteroaryl group, possibly substituted, or an acyl group, possibly substituted, and one or more of the carbon atoms in the alkyl, alkenyl, alkynyl, cycloalkyl, aryl, heteroaryl or acyl groups of $R_2$ and/or $R_3$ is optionally replaced with a heteroatom selected from the group consisting of 0, S, N, P and Si, which, where possible, is optionally substituted with one or more groups; and $R_4$ represents a hydrogen atom, a linear or branched alkyl group of any length, possibly substituted, or an alkenyl group of any length, possibly substituted, or an alkynyl group, possibly substituted, or a cycloalkyl group, possibly substituted, or an aryl group, possibly substituted.

In further embodiments, $R_2$ and $R_3$ independently or simultaneously represent an optionally substituted $C_1$-$C_{20}$ (alkyl) group, an optionally substituted $C_2$-$C_{20}$(alkenyl) group, an optionally substituted $C_2$-$C_{20}$(alkynyl) group, an optionally substituted $C_3$-$C_{20}$(cycloalkyl) group, an optionally substituted ($C_6$-$C_{14}$)-aryl group, or an optionally substituted acyl group —C(═O)—($C_1$-$C_{20}$)-alkyl.

In further embodiments, $R_2$ and $R_3$ independently or simultaneously represent an optionally substituted $C_1$-$C_{10}$ (alkyl) group, an optionally substituted $C_2$-$C_{10}$(alkenyl) group, an optionally substituted $C_2$-$C_{10}$(alkynyl) group, an optionally substituted $C_3$-$C_{10}$(cycloalkyl) group, an optionally substituted ($C_6$-$C_{10}$)-aryl group, or an optionally substituted acyl group —C(═O)—($C_1$-$C_{10}$)-alkyl.

In further embodiments, $R_2$ and $R_3$ independently or simultaneously represent an optionally substituted $C_1$-$C_6$ (alkyl) group, an optionally substituted $C_2$-$C_6$(alkenyl) group, an optionally substituted $C_2$-$C_6$(alkynyl) group, an optionally substituted $C_3$-$C_6$(cycloalkyl) group, an optionally substituted ($C_6$)-aryl group, or an optionally substituted acyl group —C(═O)—($C_1$-$C_6$)-alkyl.

In further embodiments, $R_2$ and $R_3$ independently or simultaneously represent an optionally substituted $C_1$-$C_6$ (alkyl) group, an optionally substituted $C_2$-$C_6$(alkenyl) group, an optionally substituted $C_2$-$C_6$(alkynyl) group, an optionally substituted $C_3$-$C_6$(cycloalkyl) group, an optionally substituted ($C_6$)-aryl group, or an optionally substituted acyl group —C(═O)—($C_1$-$C_6$)-alkyl.

In one embodiment, one or more of the carbon atoms in the alkyl, alkenyl, alkynyl, cycloalkyl, aryl, heteroaryl or acyl groups of $R_2$ and/or $R_3$ is optionally replaced with a heteroatom selected from the group consisting of O, S, N, P and Si, which, where possible, the heteroatom is optionally substituted with one or more groups, such as $C_1$-$C_6$(alkyl) group.

In another embodiment, $R_2$ and $R_3$ independently or simultaneously represent an optionally substituted $C_1$-$C_6$ (alkyl) group, wherein one carbon atom is replaced with a Si atom, substituted with one or more $C_1$-$C_6$(alkyl) groups. In another embodiment, $R_2$ and $R_3$ independently or simultaneously represent a —$CH_3$ group or a —$Si(CH_3)_3$ group.

In another embodiment, $R_4$ represents a hydrogen atom, an optionally substituted $C_1$-$C_{20}$(alkyl) group, an optionally substituted $C_2$-$C_{20}$(alkenyl) group, an optionally substituted $C_2$-$C_{20}$(alkynyl) group, an optionally substituted $C_3$-$C_{20}$ (cycloalkyl) group, or an optionally substituted ($C_6$-$C_{14}$)-aryl group, wherein the optional substituents are a $C_1$-$C_{20}$ (alkyl) group, a $C_2$-$C_{20}$(alkenyl) group, a $C_2$-$C_{20}$(alkynyl) group, a $C_3$-$C_{20}$(cycloalkyl) group, or a ($C_6$-$C_{14}$)-aryl group.

In another embodiment, $R_4$ represents a hydrogen atom, an optionally substituted $C_1$-$C_{10}$(alkyl) group, an optionally substituted $C_2$-$C_{10}$(alkenyl) group, an optionally substituted $C_2$-$C_{10}$(alkynyl) group, an optionally substituted $C_3$-$C_{10}$ (cycloalkyl) group, or an optionally substituted ($C_6$-$C_{10}$)-aryl group.

In another embodiment, $R_4$ represents a hydrogen atom, an optionally substituted $C_1$-$C_6$(alkyl) group, an optionally substituted $C_2$-$C_6$(alkenyl) group, an optionally substituted $C_2$-$C_6$(alkynyl) group, an optionally substituted $C_3$-$C_6$(cycloalkyl) group, or an optionally substituted ($C_6$)-aryl group.

In another embodiment, $R_4$ represents a hydrogen atom, an optionally substituted $C_1$-$C_7$(alkyl) group, substituted with an optionally substituted phenyl group.

In another embodiment, the compound of Formula (III) is

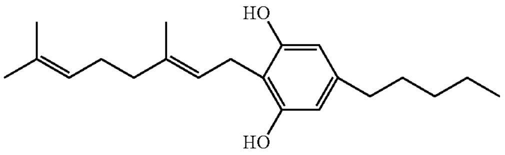
,

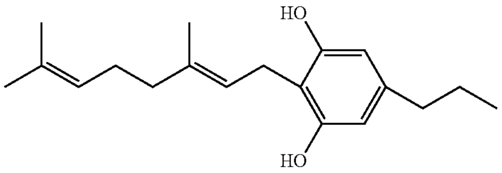
,

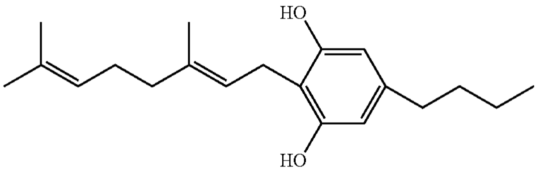
,

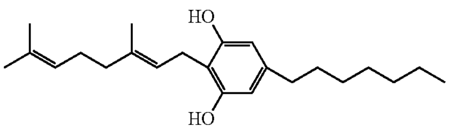
, or

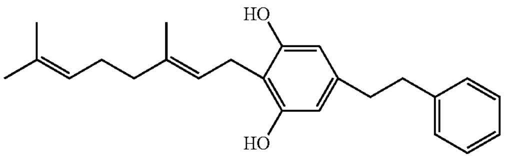
.

In another embodiment, the compound of Formula (IV) is

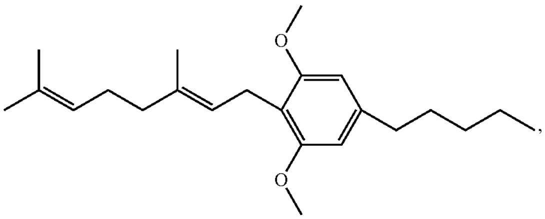
, or

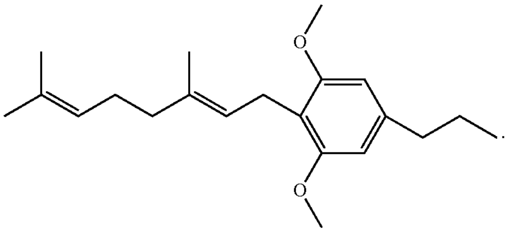
.

Carbon-carbon bond forming reactions for the preparation of cannabigerol compounds of Formula (III) or Formula (IV) include but are not limited to catalytic and non-catalytic Ullman, Suzuki-Miyaura, Negishi, Kumada, Sonogashira and Stille reactions.

In some embodiments of the invention, a compound of Formula (I) or Formula (II) is contacted with a boron containing compound such as $R_4$—$B(OH)_2$, $R_4$—$B(OR)_2$ or $R_4$—$BF_3K$; or a Grignard compound such as $R_4$—MgX; or an organozinc compound, such as $R_4$—ZnX, in the presence or absence of a catalyst to produce a compound of Formula (III) or Formula (IV). In another embodiment, the boronate group is —$B(OR)_2$, where R is H, a ($C_1$-$C_{20}$)-alkyl group, a ($C_2$-$C_{20}$)-alkenyl group, a ($C_2$-$C_{20}$)-alkynyl group, a ($C_3$-$C_{20}$)-cycloalkyl group, or a ($C_6$-$C_{14}$)-aryl group. In another embodiment, the boronate leaving group is —$B(OR)_2$, where R is H, a ($C_1$-$C_{20}$)-alkyl group (such as a ($C_1$-$C_{10}$)-alkyl group) or a ($C_6$-$C_{14}$)-aryl group (such as a ($C_6$-$C_{10}$)-aryl group). In another embodiment, the boronate leaving group is —$BF_3K$.

In one embodiment, $R_4$ represents a hydrogen atom, an optionally substituted $C_1$-$C_{20}$(alkyl) group, an optionally substituted $C_2$-$C_{20}$(alkenyl) group, an optionally substituted $C_2$-$C_{20}$(alkynyl) group, an optionally substituted $C_3$-$C_{20}$ (cycloalkyl) group, or an optionally substituted ($C_6$-$C_{14}$)-aryl group, wherein the optional substituents are a $C_1$-$C_{20}$ (alkyl) group, a $C_2$-$C_{20}$(alkenyl) group, a $C_2$-$C_{20}$(alkynyl) group, a $C_3$-$C_{20}$(cycloalkyl) group, or a ($C_6$-$C_{14}$)-aryl group.

In some embodiments of the invention, the catalytic system characterizing the process of the instant invention may comprise a base. In some embodiments, said base can be any conventional base. In some embodiments, non-limiting examples include: organic non-coordinating bases such as DBU, an alkaline or alkaline-earth metal carbonate, a carboxylate salt such as sodium or potassium acetate, or an alcoholate or hydroxide salt. Preferred bases are the alcoholate or hydroxide salts selected from the group consisting of the compounds of formula $(RO)_2M'$ and ROM", wherein M' is an alkaline-earth metal, M" is an alkaline metal (for example, NaOEt, NaOMe, $KO^iPr$, $KO^tBu$, $Mg(OEt)_2$) and R stands for hydrogen or a linear or branched alkyl group, for example a $C_1$-$C_{20}$(alkyl) group.

The catalyst can be added to the reaction medium in a large range of concentrations. As non-limiting examples, one can cite as catalyst concentration values ranging from 0.01% to 50%, relative to the amount of substrate, thus representing respectively a substrate/catalyst (S/cat) ratio of 10,000 to 2. Preferably, the complex concentration will be comprised between 0.1% and 10%, i.e. a S/cat ratio of 1,000 to 10 respectively. In some preferred embodiments, there will be used concentrations in the range of 1.0 to 5%, corresponding to a S/cat ratio of 100 to 20 respectively.

If required, useful quantities of base, added to the reaction mixture, may be comprised in a relatively large range. In some embodiments, non-limiting examples include: ranges between 1 to 100 molar equivalents relative to the substrate. However, it should be noted that it is also possible to add a small amount of base (e.g. base/substrate=1 to 3) to achieve high yields.

In the processes of this invention, the catalytic reaction can be carried out in the presence or absence of a solvent. When a solvent is required or used for practical reasons, then any solvent currently used in catalytic reactions can be used for the purposes of the invention. Non-limiting examples include aromatic solvents such as benzene, toluene or xylene, hydrocarbon solvents such as hexane or cyclohexane, ethers such as tetrahydrofuran, or yet primary or secondary alcohols, or water, or mixtures thereof. A person skilled in the art is well able to select the solvent most convenient in each case to optimize the catalytic reaction.

The temperature at which the catalytic reaction can be carried out is comprised between −30° C. and 200° C., more preferably in the range of between 0° C. and 100° C. Of course, a person skilled in the art is also able to select the preferred temperature.

Standard catalytic conditions, as used herein, typically implies the mixture of the substrate with the catalyst with or without a base, possibly in the presence of a solvent, and then treating such a mixture with the desired reactant at a chosen temperature in air or under an inert atmosphere of nitrogen or argon gas. Varying the reaction conditions, including for example, catalyst, temperature, solvent and reagent, to optimize the yield of the desired product would be well within the abilities of a person skilled in the art.

The present invention is described in the following Examples, which are set forth to aid in the understanding of the invention, and should not be construed to limit in any way the scope of the invention as defined in the claims which follow thereafter.

EXAMPLES

The disclosure will now be described in further details by way of the following examples, wherein the temperatures are indicated in degrees centigrade and the abbreviations have the usual meaning in the art.

All the procedures described hereafter have been carried out under an inert atmosphere unless stated otherwise. All preparations and manipulations under air-free conditions were carried out under $N_2$ or Ar atmospheres with the use of standard Schlenk, vacuum line and glove box techniques in dry, oxygen-free solvents. Deuterated solvents were degassed and dried over activated molecular sieves. NMR spectra were recorded on a 400 MHz spectrometer (400 MHz for $^{1}H$, 100 MHz for $^{13}C$ and 162 MHz for $^{31}P$). All $^{31}P$ chemical shifts were measured relative to 85% $H_3PO_4$ as an external reference. $^{1}H$ and $^{13}C$ chemical shifts were measured relative to partially deuterated solvent peaks but are reported relative to tetramethylsilane.

Example 1. Preparation of (E)-2-(3,7-dimethylocta-2,6-dienyl)benzene-1,3,5-triol

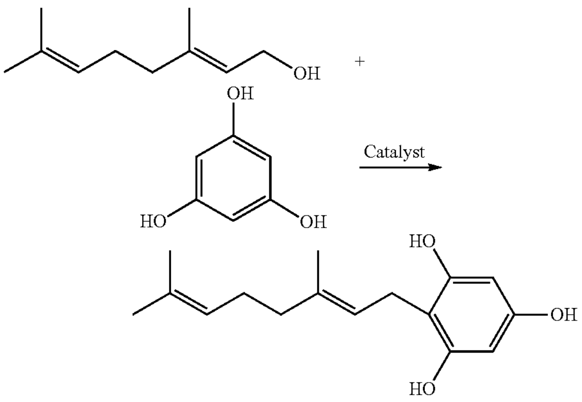

A solution of geraniol (12.24 g, 79.3 mmol) in acetonitrile (60 ml) was added slowly to a mixture of phloroglucinol (10.0 g, 79.3 mmol), $BF_3.Et_2O$ (3.68 g, 3.2 ml, 25.93 mmol), silver nitrate (140 mg, 0.82 mmol) and $MgSO_4$ (10 g) in acetonitrile (60 ml) at room temperature and the mixture stirred for 4 hours. The reaction was quenched with ice-cold water and extracted with ethyl acetate (3×50 ml). The combined organic portion was washed with $NaHCO_3$ solution, then water and dried ($MgSO_4$). It was filtered and evaporated to dryness and chromatographed on silica gel using hexanes/ethyl acetate to give the product as a yellow oil, which crystallized on standing. Yield=8.2 g.

Example 2. Preparation of (E)-4-(3,7-dimethylocta-2,6-dienyl)-3,5-dihydroxyphenyl Trifluoromethanesulfonate

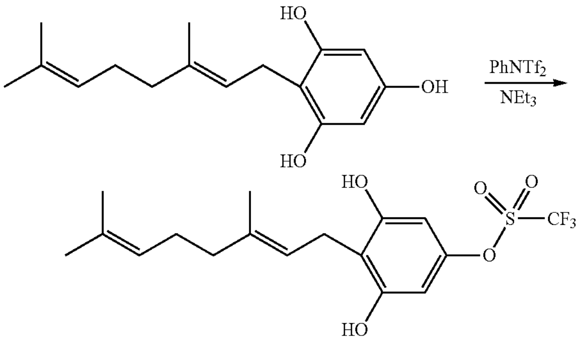

Triethylamine (4.62 g, 45.7 mmol) was added to a solution of (E)-2-(3,7-dimethylocta-2,6-dienyl)benzene-1,3,5-triol (4.0 g, 15.2 mmol) in dichloromethane (40 ml) and the mixture was cooled to 0° C. A solution of N-Phenyl-bis (trifluoromethanesulfonimide) (5.72 g, 16.0 mmol) was added slowly and the mixture allowed to warm to room temperature and stirred overnight. The reaction was quenched with water and the phases separated. The aqueous layer was extracted with dichloromethane (3×25 ml) and the combined organic layers was washed with brine and dried ($MgSO_4$). It was filtered through a pad of silica gel and the solvent removed under reduced pressure. The crude residue was chromatographed using hexanes/EA (10:1) and the product was isolated as a pale-yellow oil, which crystallized on standing. Yield=4.34 grams.

Example 3. Preparation of (E)-4-(3,7-dimethylocta-2,6-dienyl)-3,5-bis(trimethylsilyloxy)phenyl Trifluoromethanesulfonate

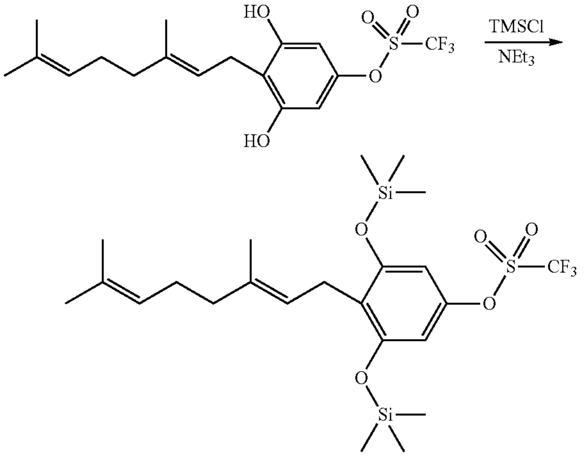

TMSCl (7.17 g, 66 mmol) was added to a mixture of (E)-4-(3,7-dimethylocta-2,6-dienyl)-3,5-dihydroxyphenyl trifluoromethanesulfonate (4.34 g, 11 mmol) and $NEt_3$ (6.67 g, 66 mmol) in $CH_2Cl_2$ (40 ml) at room temperature (water bath) under argon. The mixture was stirred at room temperature for 15 hours. It was filtered and the solvent was removed from the filtrate. It was then suspended in hexanes (40 ml) and stirred for 2 hours. It was filtered and the solvent removed under reduced pressure and the product dried under vacuum to give the product as a pale-yellow oil. Yield=4.62 g.

Example 4. Preparation of (E)-4-(3,7-dimethylocta-2,6-dienyl)-3,5-dimethoxyphenyl Trifluoromethanesulfonate

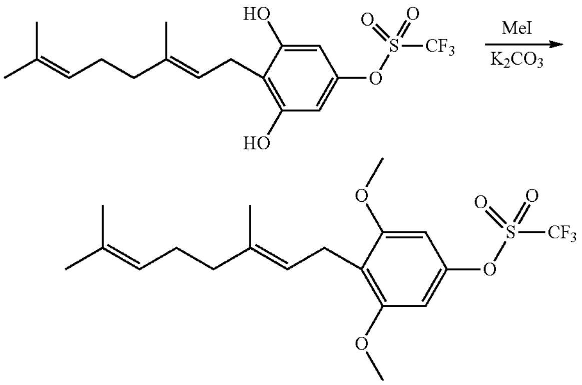

Anhydrous DMF (50 ml) was added to a mixture of (E)-4-(3,7-dimethylocta-2,6-dienyl)-3,5-dihydroxyphenyl trifluoromethanesulfonate (4.34 g, 11 mmol), methyl iodide (3.5 g, 25 mmol), and potassium carbonate (4.2 g, 30 mmol) in a Schlenk flask and the suspension stirred vigorously under argon for 12 hours at room temperature. Water (100 ml) was added, and the mixture was extracted with diethyl ether (3×50 ml). The organic layer was washed with water (2×100 ml), brine, and dried ($MgSO_4$). It was filtered and the solvent removed under reduced pressure. The residue was chromatographed using hexanes/ethyl acetate and the pure product was isolated as a pale-yellow oil. Yield=4.42 g.

Example 5. Reaction of (E)-4-(3,7-dimethylocta-2,6-dienyl)-3,5-bis(trimethylsilyloxy)phenyl Trifluoromethanesulfonate with n-Pentylzinc Bromide

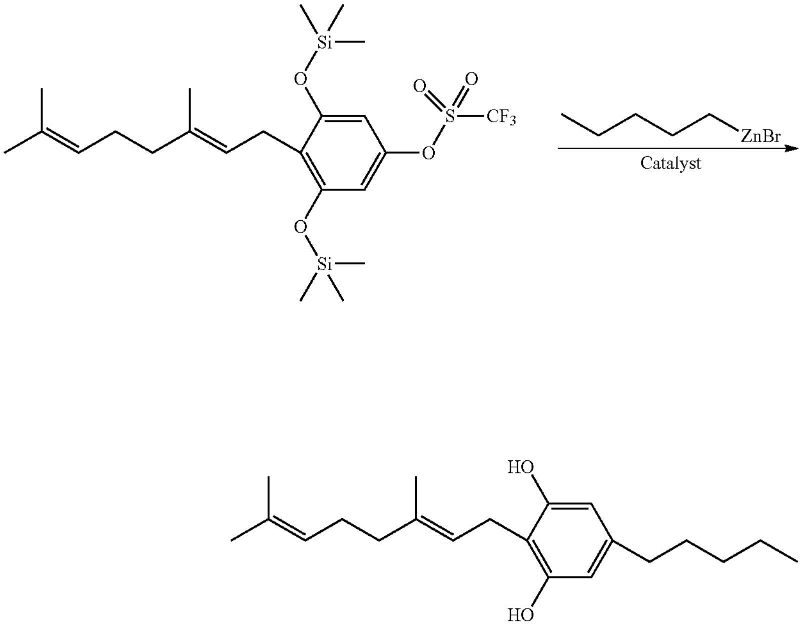

A solution of n-pentylzinc bromide (5.6 ml of a 0.5 M solution in THF, 2.78 mmol) was added to a solution of (E)-4-(3,7-dimethylocta-2,6-dienyl)-3,5-bis(trimethylsilyloxy)phenyl trifluoromethanesulfonate (1.0 g, 1.86 mmol) and $PdCl_2$(dppf) (34 mg, 0.046 mmol) in THF (2 ml) and the mixture was stirred at room temperature for 15 hours under argon. Water (5 ml) was added followed by 2M $H_2SO_4$ (2 ml) and the mixture stirred at room temperature for 1 hour. The phases were separated, and the organic layer was dried ($MgSO_4$), filtered and evaporated to dryness. The residue was dissolved in hexanes/ethyl acetate and filtered through a short pad of silica gel. The filtrate was evaporated to dryness to give a pale-yellow oil. Yield=0.42 g.

Example 6. Reaction of (E)-4-(3,7-dimethylocta-2,6-dienyl)-3,5-bis(trimethylsilyloxy)phenyl Trifluoromethanesulfonate with n-Propylzinc Bromide

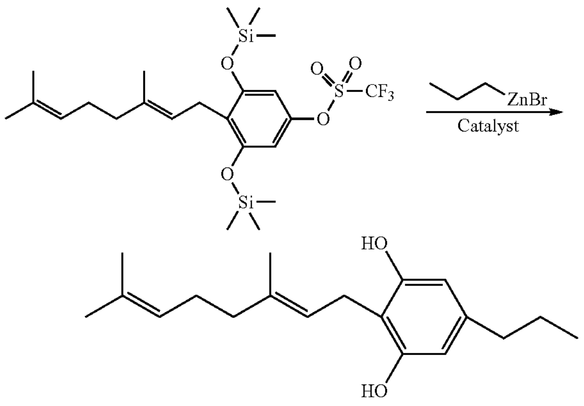

A solution of n-propylzinc bromide (5.6 ml of a 0.5 M solution in THF, 2.78 mmol) was added to a solution of (E)-4-(3,7-dimethylocta-2,6-dienyl)-3,5-bis(trimethylsilyloxy)phenyl trifluoromethanesulfonate (1.0 g, 1.86 mmol) and $PdCl_2$(dppf) (34 mg, 0.046 mmol) in THF (2 ml) and the mixture was stirred at room temperature for 15 hours under argon. Water (5 ml) was added followed by 2M $H_2SO_4$ (2 ml) and the mixture stirred at room temperature for 1 hour. The phases were separated, and the organic layer was dried ($MgSO_4$), filtered and evaporated to dryness. The residue was dissolved in hexanes/ethyl acetate and filtered through a short pad of silica gel. The filtrate was evaporated to dryness to give a pale-yellow oil. Yield=0.38 g.

Example 7. Reaction of (E)-4-(3,7-dimethylocta-2,6-dienyl)-3,5-bis(trimethylsilyloxy)phenyl Trifluoromethanesulfonate with n-Butylzinc Bromide

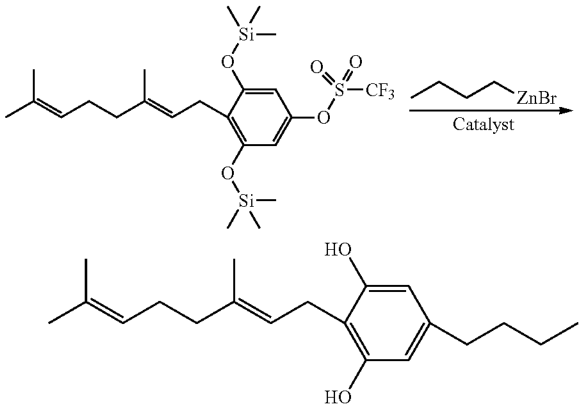

A solution of n-butylzinc bromide (5.6 ml of a 0.5 M solution in THF, 2.78 mmol) was added to a solution of (E)-4-(3,7-dimethylocta-2,6-dienyl)-3,5-bis(trimethylsilyloxy)phenyl trifluoromethanesulfonate (1.0 g, 1.86 mmol) and $PdCl_2$(dppf) (34 mg, 0.046 mmol) in THF (2 ml) and the mixture was stirred at room temperature for 15 hours under argon. Water (5 ml) was added followed by 2M $H_2SO_4$ (2 ml) and the mixture stirred at room temperature for 1 hour. The phases were separated, and the organic layer was dried ($MgSO_4$), filtered and evaporated to dryness. The residue was dissolved in hexanes/ethyl acetate and filtered through a short pad of silica gel. The filtrate was evaporated to dryness to give a pale-yellow oil. Yield=0.41 g.

Example 8. Reaction of (E)-4-(3,7-dimethylocta-2,6-dienyl)-3,5-bis(trimethylsilyloxy)phenyl Trifluoromethanesulfonate with n-Heptylzinc Bromide

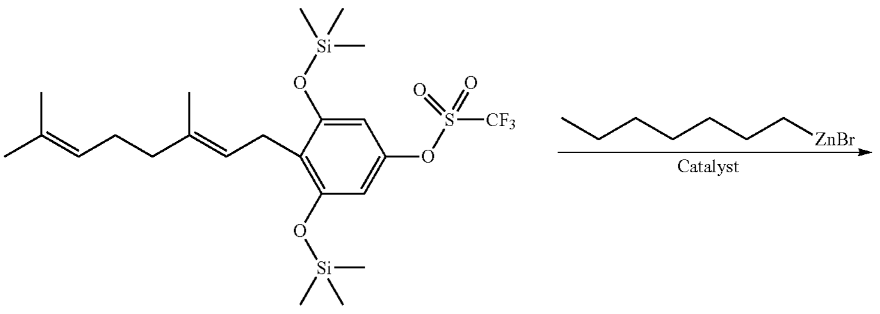

-continued

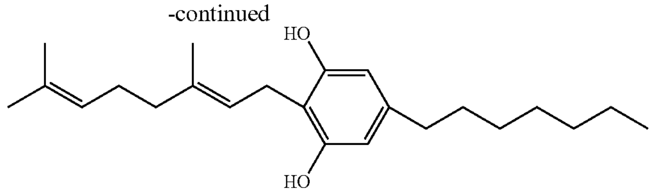

A solution of n-heptylzinc bromide (5.6 ml of a 0.5 M solution in THF, 2.78 mmol) was added to a solution of (E)-4-(3,7-dimethylocta-2,6-dienyl)-3,5-bis(trimethylsilyloxy)phenyl trifluoromethanesulfonate (1.0 g, 1.86 mmol) and $PdCl_2$(dppf) (34 mg, 0.046 mmol) in THF (2 ml) and the mixture was stirred at room temperature for 15 hours under argon. Water (5 ml) was added followed by 2M $H_2SO_4$ (2 ml) and the mixture stirred at room temperature for 1 hour. The phases were separated, and the organic layer was dried ($MgSO_4$), filtered and evaporated to dryness. The residue was dissolved in hexanes/ethyl acetate and filtered through a short pad of silica gel. The filtrate was evaporated to dryness to give a pale-yellow oil. Yield=0.45 g.

Example 9. Reaction of (E)-4-(3,7-dimethylocta-2,6-dienyl)-3,5-dimethoxyphenyl Trifluoromethanesulfonate with n-Pentylzinc Bromide

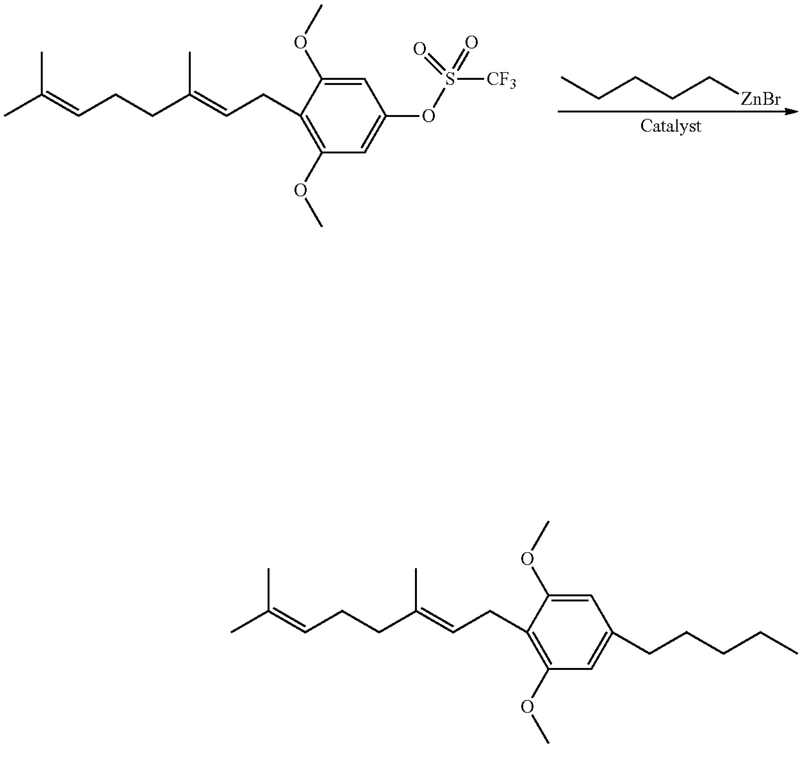

A solution of n-pentylzinc bromide (5.0 ml of a 0.5 M solution in THF, 2.50 mmol) was added to a mixture of (E)-4-(3,7-dimethylocta-2,6-dienyl)-3,5-dimethoxyphenyl trifluoromethanesulfonate (1.0 g, 2.37 mmol) and $PdCl_2$(dppf) (40 mg, 0.06 mmol) and the mixture stirred at room temperature for 15 hours under argon. It was quenched with ammonium chloride solution and diethyl ether added. The phases were separated, and the organic layer was dried ($MgSO_4$), filtered and evaporated to dryness. Flash chromatography using hexanes/ethyl acetate yielded the product as a pale-yellow oil. Yield=0.68 g.

Example 10. Reaction of (E)-4-(3,7-dimethylocta-2,6-dienyl)-3,5-dimethoxyphenyl Trifluoromethanesulfonate with n-Propylzinc Bromide

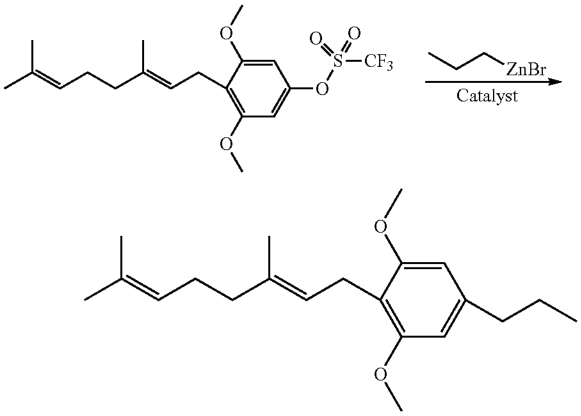

A solution of n-propylzinc bromide (5.0 ml of a 0.5 M solution in THF, 2.50 mmol) was added to a mixture of (E)-4-(3,7-dimethylocta-2,6-dienyl)-3,5-dimethoxyphenyl trifluoromethanesulfonate (1.0 g, 2.37 mmol) and $PdCl_2$(dppf) (40 mg, 0.06 mmol) and the mixture stirred at room temperature for 15 hours under argon. It was quenched with ammonium chloride solution and diethyl ether added. The phases were separated, and the organic layer was dried ($MgSO_4$), filtered and evaporated to dryness. Flash chromatography using hexanes/ethyl acetate yielded the product as a pale-yellow oil. Yield=0.65 g.

Example 11. Reaction of (E)-4-(3,7-dimethylocta-2,6-dienyl)-3,5-bis(trimethylsilyloxy)phenyl Trifluoromethanesulfonate with Phenethylzinc Bromide

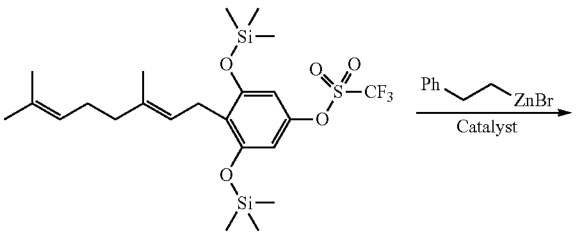

-continued

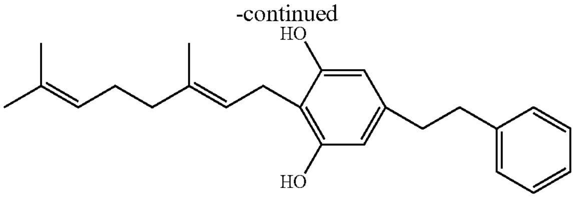

A solution of n-phenethylzinc bromide (5.6 ml of a 0.5 M solution in THF, 2.78 mmol) was added to a solution of (E)-4-(3,7-dimethylocta-2,6-dienyl)-3,5-bis(trimethylsilyloxy)phenyl trifluoromethanesulfonate (1.0 g, 1.86 mmol) and $PdCl_2$(dppf) (34 mg, 0.046 mmol) in THF (2 ml) and the mixture was stirred at 40° C. for 15 hours under argon. Water (5 ml) was added followed by 2M $H_2SO_4$ (2 ml) and the mixture stirred at room temperature for 1 hour. The phases were separated, and the organic layer was dried ($MgSO_4$), filtered and evaporated to dryness. The residue was dissolved in hexanes/hexanes and filtered through a short pad of silica gel. The filtrate was evaporated to dryness to give a pale-yellow oil. Yield=0.48 g.

While the foregoing invention has been described in some detail for purposes of clarity and understanding, it will be appreciated by one skilled in the art, from a reading of the disclosure, that various changes in form and detail can be made without departing from the true scope of the invention in the appended claims.

All publications, patents, and patent applications are herein incorporated by reference in their entirety to the same extent as if each individual publication, patent or patent application was specifically and individually indicated to be incorporated by reference in its entirety.

What is claimed is:

1. A compound of Formula (I):

(I)

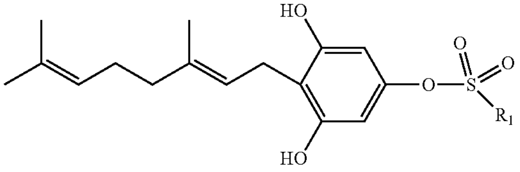

wherein, $R^1$ is selected from the group consisting of a hydrogen atom, a linear or branched optionally substituted alkyl group, an optionally substituted alkenyl group, an optionally substituted alkynyl group, an optionally substituted cycloalkyl group, an optionally substituted aryl group, an optionally substituted heteroaryl group, and an optionally substituted $OR^c$ group or an $NR^c_2$ group, wherein $R^1$ is optionally substituted by a substituent selected from the group consisting of halogen atoms, $OR^c$, and $NR^c_2$ groups, wherein $R^c$ is a hydrogen atom or a cyclic, linear or branched alkyl, aryl or alkenyl group; or a stereoisomer thereof.

2. The compound of Formula (I) according to claim 1, wherein $R^1$ is selected the group consisting of a hydrogen atom, an optionally substituted $C_1$-$C_{20}$(alkyl) group, an optionally substituted $C_2$-$C_{20}$(alkenyl) group, an optionally substituted $C_2$-$C_{20}$(alkynyl) group, an optionally substituted $C_3$-$C_{20}$(cycloalkyl) group, an optionally substituted ($C_6$-$C_{14}$)-aryl group, an optionally substituted ($C_5$-$C_{14}$)-heteroaryl group, an $OR^c$ group, and an $NR^c_2$ group, wherein $R^c$ selected from the group consisting of is hydrogen, $C_1$-$C_{20}$ (alkyl), $C_2$-$C_{20}$(alkenyl), $C_1$-$C_{20}$(alkynyl), $C_3$-$C_{20}$(cycloalkyl) and ($C_6$-$C_{14}$)-aryl, and wherein the optional substituents on each of the above groups are selected from halogen.

3. The compound of Formula (I) according to claim 2, wherein $R^1$ represents is selected from the group consisting of a hydrogen atom, an optionally substituted $C_1$-$C_{10}$(alkyl) group, an optionally substituted $C_2$-$C_{10}$(alkenyl) group, an optionally substituted $C_2$-$C_{10}$(alkynyl) group, an optionally substituted $C_3$-$C_{10}$(cycloalkyl) group, an optionally substituted ($C_6$-$C_{10}$)-aryl group, an optionally substituted ($C_5$-$C_{10}$)-heteroaryl group, an $OR^c$ group, and an $NR^c_2$ group.

4. The compound of Formula (I) according to claim 1, wherein $R^1$ is selected from the group consisting of a hydrogen atom and an optionally substituted $C_1$-$C_6$(alkyl) group, and or a halo-substituted $C_1$-$C_6$(alkyl) group.

5. The compound of Formula (I) according to claim 1, wherein $R^c$ is selected from the group consisting of hydrogen, $C_1$-$C_{10}$(alkyl), $C_2$-$C_{10}$(alkenyl), $C_1$-$C_{10}$(alkynyl), $C_3$-$C_{10}$(cycloalkyl), and ($C_6$-$C_{10}$)-aryl.

6. The compound of Formula (I) according to claim 1, wherein the compound is

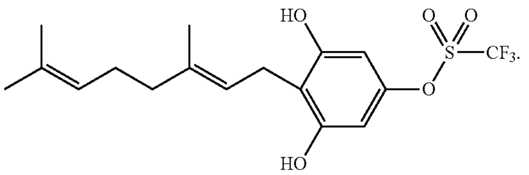 [SMILES: CC(C)=CCC/C(C)=C/Cc1c(O)cc(OS(=O)(=O)C(F)(F)F)cc1O]

* * * * *